US007901626B2

(12) United States Patent
Kawahara et al.

(10) Patent No.: US 7,901,626 B2
(45) Date of Patent: Mar. 8, 2011

(54) FLUID HANDLING UNIT AND FLUID HANDLING APPARATUS USING SAME

(75) Inventors: Noriyuki Kawahara, Saitama (JP); Kyouhei Yamada, Saitama (JP); Satoshi Ikeya, Saitama (JP)

(73) Assignee: Enplas Corporation, Saitama (JP)

( * ) Notice: Subject to any disclaimer, the term of this patent is extended or adjusted under 35 U.S.C. 154(b) by 362 days.

(21) Appl. No.: 12/118,876

(22) Filed: May 12, 2008

(65) Prior Publication Data

US 2008/0293129 A1 Nov. 27, 2008

(30) Foreign Application Priority Data

May 23, 2007 (JP) ................................ 2007-137101
Jan. 21, 2008 (JP) ................................ 2008-009997

(51) Int. Cl.

| | |
|---|---|
| ***G01N 15/06*** | (2006.01) |
| ***G01N 33/00*** | (2006.01) |
| ***G01N 33/48*** | (2006.01) |
| ***G01N 1/10*** | (2006.01) |
| ***B01L 3/00*** | (2006.01) |
| ***C12M 1/34*** | (2006.01) |
| ***C12M 3/00*** | (2006.01) |

(52) U.S. Cl. .......... 422/68.1; 422/99; 422/102; 436/180; 435/287.2; 435/288.4

(58) Field of Classification Search ....................... None
See application file for complete search history.

(56) References Cited

U.S. PATENT DOCUMENTS 4,623,461 A * 11/1986 Hossom et al. ............... 210/445
5,096,676 A * 3/1992 McPherson et al. .......... 422/102

(Continued)

FOREIGN PATENT DOCUMENTS

EP 0791394 A2 8/1997

(Continued)

OTHER PUBLICATIONS

English Language Abstract from esp@cenet for JP 9101302.

(Continued)

*Primary Examiner* — Jill Warden
*Assistant Examiner* — Charles Hammond
(74) *Attorney, Agent, or Firm* — Bachman & LaPointe, P.C.

(57) ABSTRACT

A fluid handling unit 16 has an outside large-diameter cylindrical portion 16*a*, an outside small-diameter cylindrical portion 16*b* and an inside cylindrical portion 16*c*, which are integral-molded so as to be integrated with each other. The inside cylindrical portion 16*c* has a plurality of slits 16*d*, which are extend from the lower end of the inside cylindrical portion 16*c* to the upper end thereof, for establishing a communication between an inside fluid housing chamber 30, which is formed in the inside cylindrical portion 16*c*, and an outside fluid housing chamber 28 which is formed between the inside cylindrical portion 16*c* and the outside small-diameter cylindrical portion 16*b*. The plurality of slits 16*d* are designed to cause the most part of a liquid in the inside fluid housing chamber 30 to enter the outside fluid housing chamber 28 due to capillarity when the quantity of the liquid fed into the fluid handling unit 16 is not larger than a predetermined quantity, and to allow the liquid in the outside fluid housing chamber 28 to enter the inside fluid housing chamber when the quantity of the liquid fed into the fluid handling unit 16 exceeds the predetermined quantity.

24 Claims, 11 Drawing Sheets

U.S. PATENT DOCUMENTS

| | | | | |
|---|---|---|---|---|
| 5,462,881 | A * | 10/1995 | Perlman | 436/180 |
| 5,650,125 | A * | 7/1997 | Bosanquet | 422/102 |
| 6,083,761 | A | 7/2000 | Kedar et al. | |
| 7,556,778 | B2 * | 7/2009 | Kawahara et al. | 422/102 |
| 7,662,345 | B2 * | 2/2010 | Kawahara et al. | 422/101 |

FOREIGN PATENT DOCUMENTS

| | | | |
|---|---|---|---|
| EP | 1547686 | A1 | 6/2005 |
| EP | 1785725 | A2 | 5/2007 |
| JP | 9-101302 | A | 4/1997 |
| JP | 9-159673 | A | 6/1997 |
| JP | 2001004628 | A | 1/2001 |

OTHER PUBLICATIONS

English Language Abstract from esp@cenet for JP 9159673.
English Language Abstract from esp@cenet for JP2001004628.

* cited by examiner

FLUID HANDLING UNIT AND FLUID HANDLING APPARATUS USING SAME

BACKGROUND OF THE INVENTION

1. Field of the Invention

The present invention generally relates to a fluid handling unit and a fluid handling apparatus using the same. More specifically, the invention relates to a fluid handling unit capable of being used as a part of a sample analyzing apparatus for analyzing samples, such as biosubstances representative of functional substances, and a fluid handling apparatus using the same.

2. Description of the Prior Art

As conventional methods for specifically detecting biosubstances, such as proteins, there are known various methods for causing an antigen-antibody reaction using an antibody to a specific biosubstance, to carry out the visual recognition or spectroscopic measurement of a reactant thus obtained, to detect the biosubstance.

As methods for quantifying a reactant obtained by an antigen-antibody reaction of a biosubstance, such as a protein, there are widely adopted some methods, such as ELISA (Enzyme-Linked ImmunoSorbent Assay). In these methods, there is used a sample analyzing apparatus called a microplate wherein a large number of fine recessed portions generally called microwells (which will be hereinafter referred to as "wells") are arrayed. The wall surfaces of the wells are coated with an antibody to a specific biosubstance, which is a target substance, as a capturing (or catching) material, to capture (or catch) the target substance by the capturing material to detect the target substance by measuring a reactant, which is obtained by an antigen-antibody reaction between the target substance and the antibody, by fluorescence, luminous reagents or the like.

In a typical method using a microplate, such as ELISA, a well is filled with a liquid, such as a specimen containing a target substance or an antibody reagent, as a reaction solution to cause a reaction. This reaction does not occur until the components in the liquid filled in the well are moved by molecular diffusion to reach the bottom and inner walls of the well. For that reason, if a microplate is allowed to stand, a theoretical reaction time depends on the diffusion time of the components in the liquid filled in the well. Since the molecules in the liquid move while colliding with the surrounding molecules, the speed of diffusion is very slow. If the target substance is a protein having a molecular weight of about 70,000, the speed of diffusion is about 0.5 to $1\times10^{-6}$ $cm^2/sec$ in a dilute aqueous solution (room temperature). Therefore, in the liquid filled in the well, the target substance located apart from the bottom and inner walls of the well is hardly allowed to react in a practical measuring time. In addition, since it is effective to cause the bottom and wall surfaces in the well serving as a reacting portion to uniformly contact the reaction solution in order to improve the efficiency of reaction in a microplate, it is required to use a larger quantity of liquid than the quantity of liquid required for the reaction.

Thus, in the conventional method using the microplate, such as ELISA, the antigen-antibody reaction proceeds only on the wall surface of the well coated with the capturing antibody. Therefore, the liquid must be allowed to stand until the reaction occurs after the target substance, antibody and substrate contained in the liquid fed into the well are suspended, circulated and sink to reach the wall surface of the well, so that there is a problem in that the efficiency of reaction is bad. In addition, in a microplate which is subdivided into a large number of wells, the quantity of liquid fed into each of the wells is limited, so that there is a problem in that the sensitivity of measurement is deteriorated.

In order to improve the sensitivity of measurement and shorten the measuring time in ELISA or the like, there is proposed a microplate capable of increasing the surface area of a reaction surface (capturing surface) to enhance the sensitivity of measurement by forming fine irregularities on the bottom face of each of wells serving as the reaction surface (see, e.g., Japanese Patent Laid-Open No. 9-159673). There is also proposed a microchip capable of increasing the surface area of a reaction surface to enhance the efficiency of reaction in a fine space by arranging a fine solid particle (bead) as a reaction solid phase in a microchannel of the microchip (see, e.g., Japanese Patent Laid-Open No. 2001-4628). Moreover, there is proposed a microplate capable of increasing the surface area of a reaction surface and saving the quantity of samples by forming a small-diameter recessed portion in the central portion of the bottom of each of wells. (see, e.g., Japanese Patent Laid-Open No. 9-101302).

However, in the microplate proposed in Japanese Patent Laid-Open No. 9-159673, there is a problem in that it is not possible to improve the efficiency of reaction although it is possible to improve the sensitivity of measurement. In addition, the microchip proposed in Japanese Patent Laid-Open No. 2001-4628 is not suitable for the measurement of a large number of specimens although it is possible to improve the efficiency of reaction, since it is a microchip having a microchannel structure, not a microplate typically used in ELISA or the like. Moreover, in the microplate proposed in Japanese Patent Laid-Open No. 9-101302, it is not possible to sufficiently improve the efficiency of reaction and the sensitivity of measurement, although it is possible to increase the surface area of the reaction surface to some extent to improve the efficiency of reaction and the sensitivity of measurement.

SUMMARY OF THE INVENTION

It is therefore an object of the present invention to eliminate the aforementioned problems and to provide a fluid handling unit for use in a fluid handling apparatus which is capable of improving the efficiency of reaction and the sensitivity of measurement with a simple structure and of shortening a reaction time and a measuring time, when the apparatus is used as a sample analyzing apparatus for measuring a large number of specimens, and a fluid handling apparatus using the same.

It is another object of the present invention to allow the above described fluid handling unit or fluid handling apparatus using the same to further improve the accuracy of analysis even if the quantity of a reagent or specimen for use in analysis is very small.

In order to accomplish the aforementioned and other objects, according to one aspect of the present invention, a fluid handling unit comprises: an container body having a bottom portion and a side portion for forming a fluid housing section therein, the container body having an opening at an upper end thereof; a partition wall portion which extends from the bottom portion for dividing the fluid housing section of the container body into a first fluid housing chamber and a second fluid housing chamber; and a communication passage which passes through the partition wall portion to establish a communication between the first fluid housing chamber and the second fluid housing chamber, wherein the communication passage is associated with the first and second fluid housing chambers for causing a liquid in the first fluid housing chamber to enter the second fluid housing chamber due to capillarity while preventing the liquid in the second fluid housing chamber from entering the first fluid housing chamber when the quantity of the liquid fed into the fluid housing section from the opening of the container body is not larger than a predetermined quantity, and for allowing the liquid in the second fluid housing chamber to enter the first fluid housing chamber when the quantity of the liquid fed to the fluid housing section from the opening of the container body exceeds the predetermined quantity.

In this fluid handling unit, the height of the partition wall portion is preferably lower than the height of the side face portion of the container body. The communication passage preferably comprises one or a plurality of slits which pass through the partition wall portion and which extend from the bottom end of the partition wall portion to the upper end thereof.

In the above described fluid handling unit, the first fluid housing chamber is preferably surrounded by the second fluid housing chamber. In this case, the container body preferably has a substantially cylindrical shape, and the partition wall portion preferably has a substantially cylindrical shape which is substantially coaxial with the container body. The container body preferably has a substantially cylindrical large-diameter portion and a substantially cylindrical small-diameter portion which is arranged below the substantially cylindrical large-diameter portion, and the partition wall portion is preferably arranged inside of the substantially cylindrical small-diameter portion. The communication passage preferably comprises a plurality of slits which are arranged at regular intervals in circumferential directions of the partition wall portion. The partition wall portion preferably has an upper end face which is inclined inwardly downwards.

In the above described fluid handling unit, the bottom face portion of the second fluid housing chamber is preferably inclined downwards as a distance from the first fluid housing chamber decreases, and the height of the lowest portion of the bottom face portion of the second fluid housing chamber is preferably substantially equal to the height of that of the first fluid housing chamber. The width of each of the slits on the side of the first fluid housing chamber is preferably larger than that on the side of the second fluid housing chamber. The most part of the liquid in the first fluid housing chamber preferably enters the second fluid housing chamber when the quantity of the liquid fed into the fluid housing section from the opening of the container body is not larger than the predetermined quantity. The fluid handling unit is preferably integral-molded.

In the above described fluid handling unit, the communication passage preferably causes the liquid in the first fluid housing chamber to enter the second fluid housing chamber while preventing the liquid in the second fluid housing chamber from entering the first fluid housing chamber, by a difference between a capillary force exerted in the first fluid housing chamber and a capillary force exerted in the second fluid housing chamber, when the quantity of the liquid fed into the fluid housing section from the opening of the container body is not larger than the predetermined quantity. In this case, the capillary force exerted in the second fluid housing chamber is preferably greater than the capillary force exerted in the first fluid housing chamber.

According to another aspect of the present invention, a fluid handling apparatus comprises: an apparatus body; and a plurality of fluid handling units arranged on the apparatus body, wherein each of the plurality of fluid handling units is the above described fluid handling unit.

In this fluid handling apparatus, the plurality of fluid handling units are preferably arranged on the apparatus body as a matrix. In this case, the plurality of fluid handling units, together with the apparatus body, may be integral-molded. The apparatus body preferably comprises a frame and a plurality of supporting members substantially arranged on the frame in parallel, and the plurality of fluid handling units are preferably arranged on each of the supporting members at regular intervals in a row. In this case, the plurality of fluid handling units, together with each of the supporting member, may be integral-molded.

According to the present invention, it is possible to provide a fluid handling unit which is capable of improving the efficiency of reaction and the sensitivity of measurement with a simple structure and of shortening a reaction time and a measuring time, and a fluid handling apparatus using the same, when the apparatus is used as a sample analyzing apparatus for measuring a large number of specimens.

It is also possible to allow the fluid handling unit or fluid handling apparatus using the same to further improve the accuracy of analysis even if the quantity of a reagent or specimen for use in analysis is very small.

BRIEF DESCRIPTION OF THE DRAWINGS

The present invention will be understood more fully from the detailed description given herebelow and from the accompanying drawings of the preferred embodiments of the invention. However, the drawings are not intended to imply limitation of the invention to a specific embodiment, but are for explanation and understanding only.

In the drawings.

DESCRIPTION OF THE PREFERRED EMBODIMENTS

Referring now to the accompanying drawings, the preferred embodiments of a fluid handling unit and a fluid handling apparatus using the same according to the present invention will be described below in detail.

Figure 1:
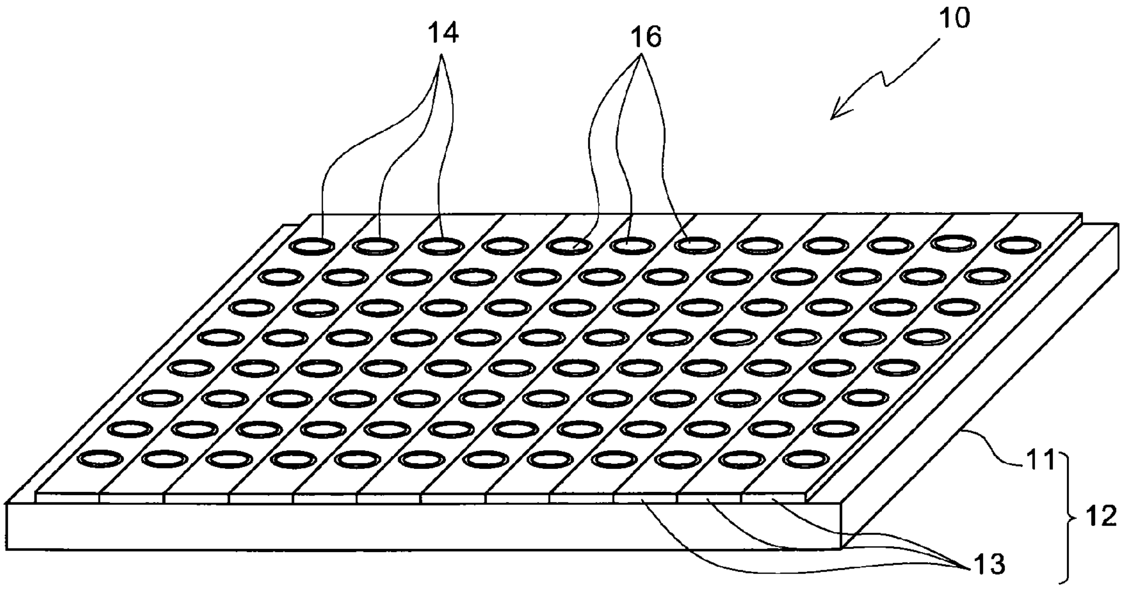
FIG. 1 is a perspective view of the preferred embodiment of a fluid handling apparatus according to the present invention.

FIGS. 1 through 9B show the preferred embodiment of a fluid handling unit and a fluid handling apparatus according to the present invention. For example, the fluid handling apparatus 10 in this preferred embodiment can be used as an apparatus for analyzing a sample containing a biosubstance, such as a protein, which is representative of functional substances. In general, the fluid handling apparatus 10 can be used as a sample analyzing apparatus called a microwell plate for carrying out the measurement of a large number of specimens. As shown in FIG. 1, the fluid handling apparatus 10 comprises: an apparatus body 12; and a plurality of fluid handling units 16 (96 (=8×12) fluid handling units in this preferred embodiment) mounted on the apparatus body 12 so as to be arranged as a matrix.

Figure 2:
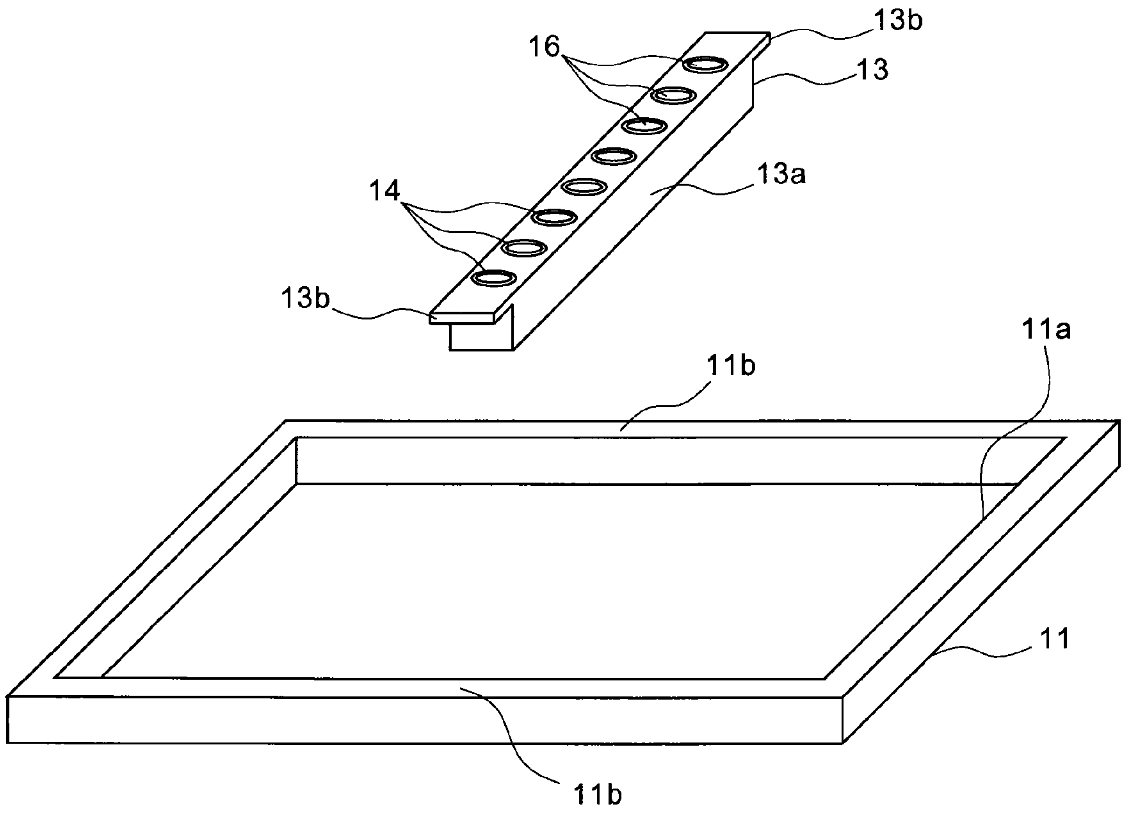
FIG. 2 is a perspective view showing a frame and a fluid handling unit supporting member of the apparatus body of the fluid handling apparatus of FIG. 1.

As shown in FIGS. 1 and 2, the apparatus body 12 is made of a resin material, such as polystyrene (PS), polycarbonate (PC) or polymethyl methacrylate (PMMA), or a glass material, and comprises: a substantially rectangular frame 11 which has a substantially rectangular through hole 11*a* in the center thereof and which has a thickness of a few millimeters, the length of each side of the frame 11 being in the range of from a few centimeters to over ten centimeters; and a plurality of fluid handling unit supporting members 13 (12 fluid handling unit supporting members in this preferred embodiment) mounted on the frame 11. Furthermore, the through hole 11*a* of the frame 11 may be replaced with a recessed portion with bottom. Alternatively, the frame 11 may be a standard frame, such as a frame for microplate of SBS (Society for Biomolecular Screening) standard. The fluid handling unit supporting members 13 may be made of a transparent material. However, if the fluid handling apparatus 10 in this preferred embodiment is used for measuring fluorescence, the fluid handling unit supporting members 13 is preferably made of a member (e.g., a black member) which is difficult to allow light to pass through the member in order to suppress the rise of background during the measurement of fluorescence.

As shown in FIG. 2, each of the fluid handling unit supporting members 13 comprises: an elongated supporting member body 13*a* having a shape of substantially rectangular parallelepiped, the length of which is substantially equal to the width of the through hole 11*a* of the frame 11; and a pair of substantially rectangular protruding portions 13*b* which protrude from the upper portions of the supporting member body 13*a* at both ends in longitudinal directions to extend along the upper surface of the supporting member body 13*a*. As shown in FIG. 1, the supporting member bodies 13*a* of the fluid handling unit supporting members 13 are inserted into the through hole 11*a* of the frame 11 to be mounted on the frame 11 substantially in parallel and adjacent to each other so that the protruding portions 13*b* are supported on a pair of upper surfaces 11*b* of the frame 11 extending in longitudinal directions. Thus, the apparatus body 12 is assembled.

Figure 3:
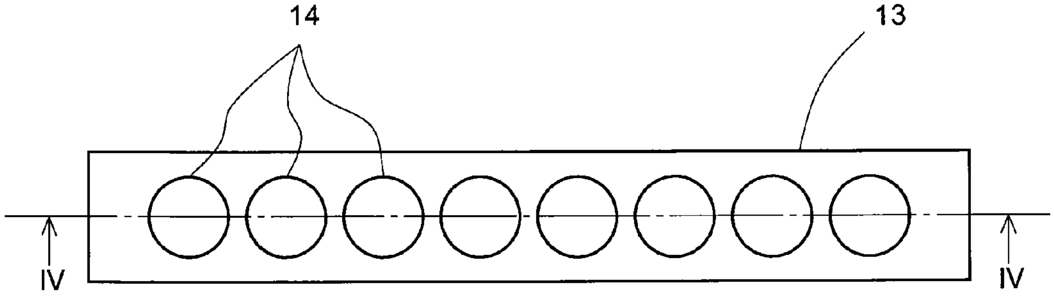
FIG. 3 is an enlarged plan view of the fluid handling unit supporting member of FIG. 2.
Figure 4:
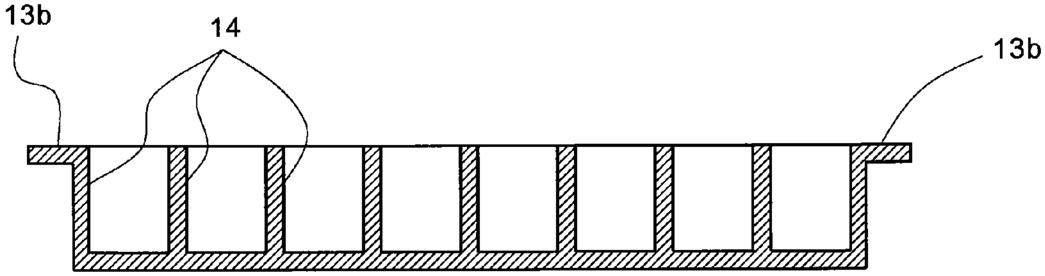
FIG. 4 is a sectional view taken along line IV-IV of FIG. 3.
Figure 5:
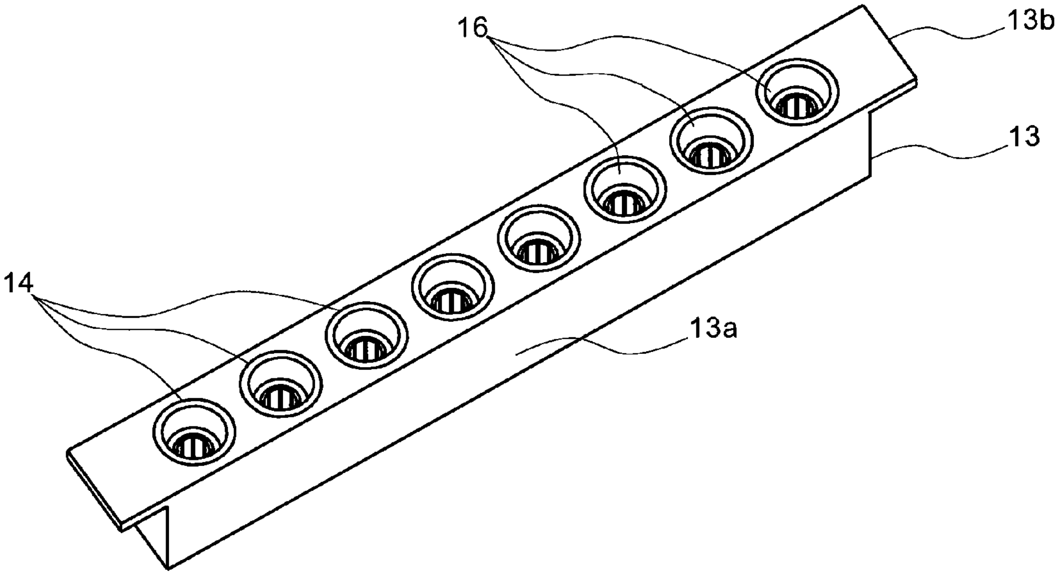
FIG. 5 is a perspective view showing a state that fluid handling units are mounted on the fluid handling unit supporting member of FIG. 2.

As shown in FIGS. 3 and 4, a plurality of substantially cylindrical recessed portions 14 (eighth recessed portions 14 in this preferred embodiment) (which will be hereinafter referred to as "mounting recessed portions 14") having a diameter and depth of a few millimeters are formed in the upper surface of the supporting member body 13*a* of each of the fluid handling unit supporting members 13 so as to be arranged at regular intervals in a row. In each of the mounting recessed portions 14, one of the fluid handling units 16 is mounted as shown in FIG. 5.

Figure 6:
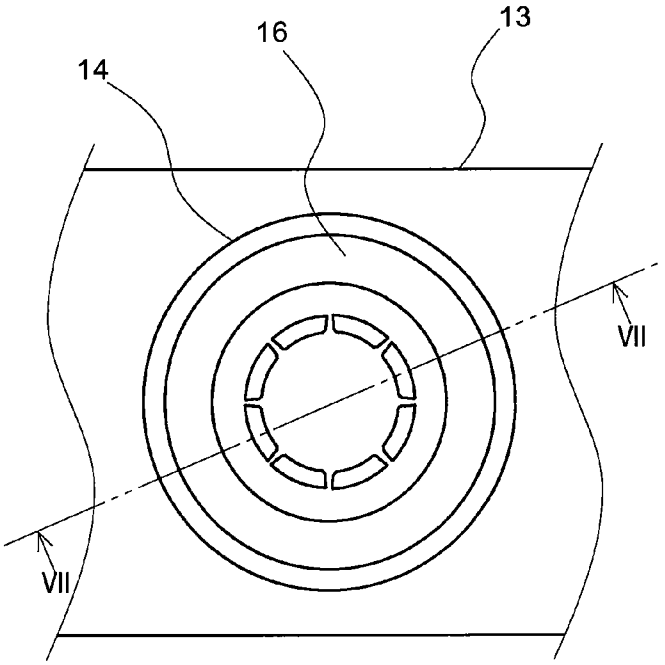
FIG. 6 is an enlarged plan view of one of the fluid handling units, each of which is mounted in corresponding one of mounding recessed portions of the fluid handling apparatus of FIG. 1.
Figure 7:
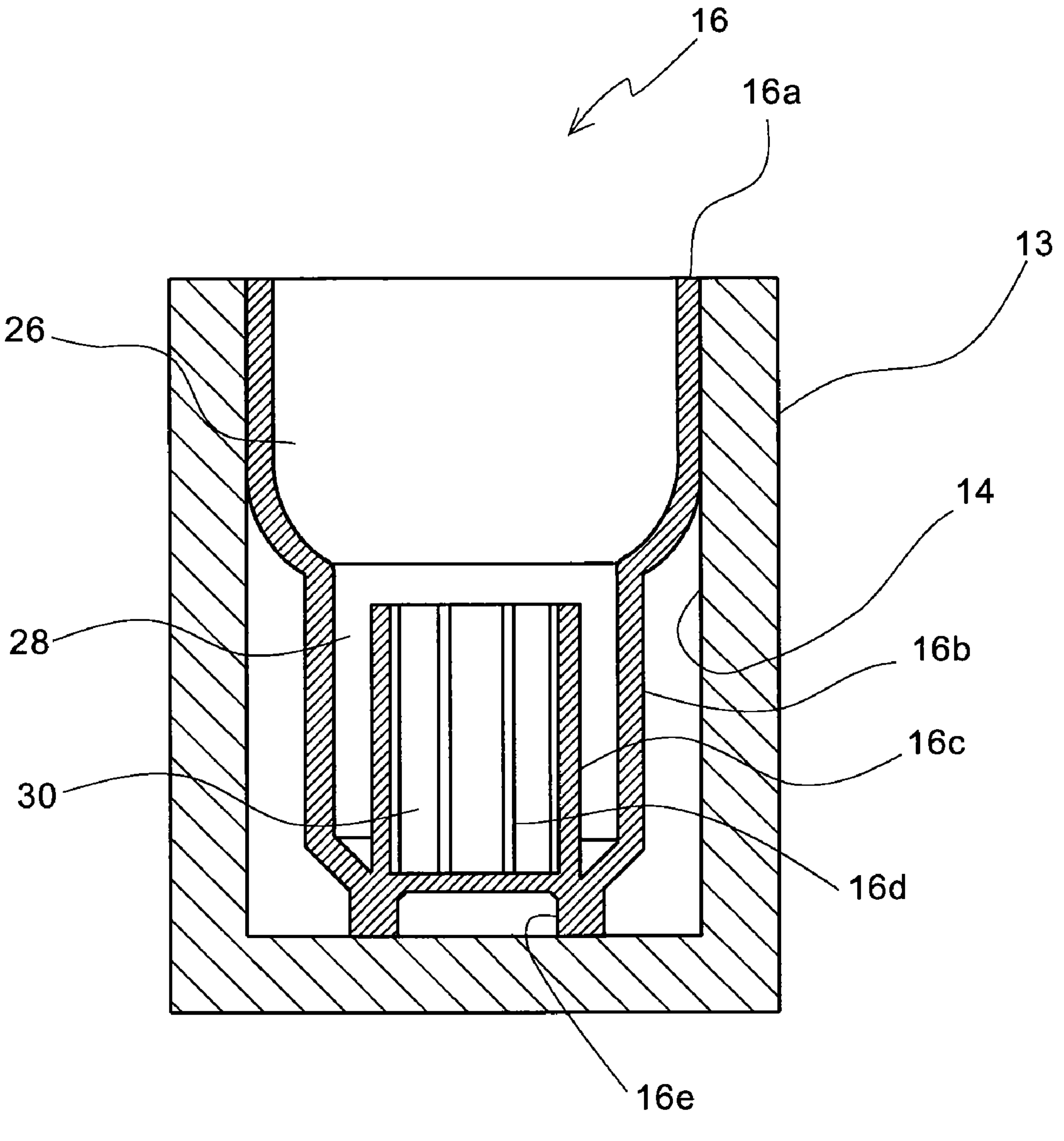
FIG. 7 is a sectional view taken along line VII-VII of FIG. 6.
Figure 8A:
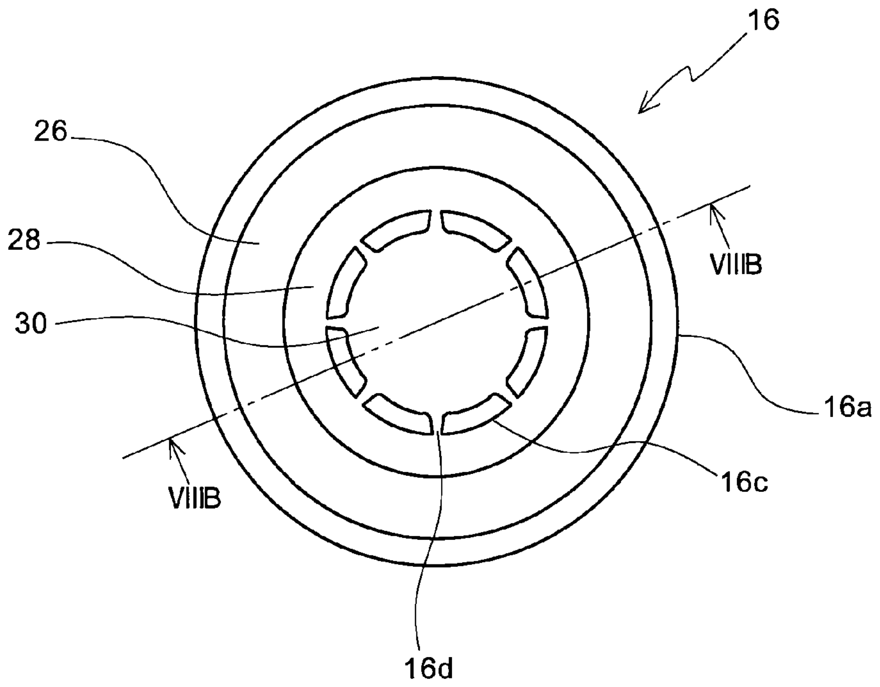
FIG. 8A is an enlarged plan view of one of the fluid handling units of the fluid handling apparatus of FIG. 1.
Figure 8B:
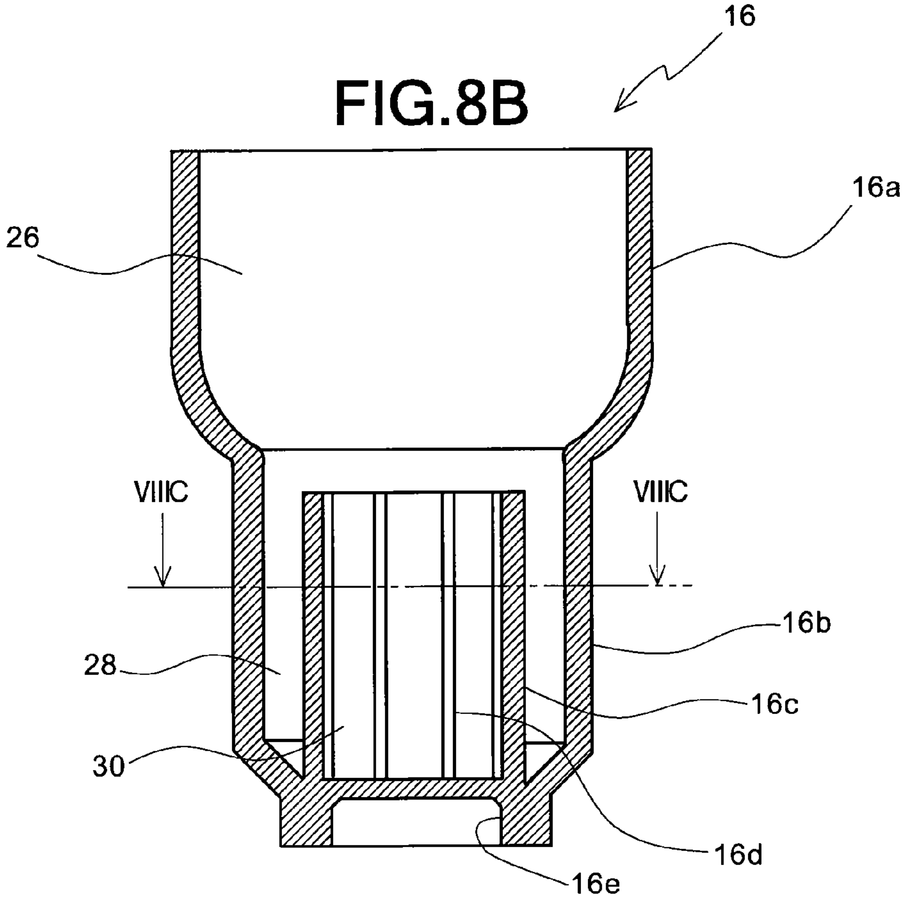
FIG. 8B is a sectional view taken along line VIIIB-VIIIB of FIG. 8A.
Figure 8C:
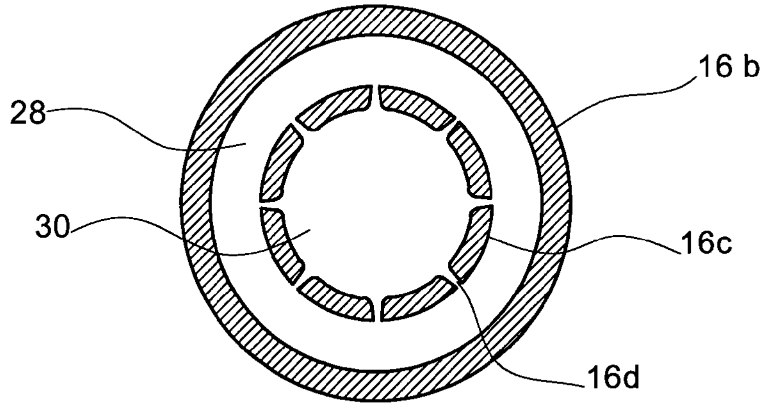
FIG. 8C is a sectional view taken along line VIIIC-VIIIC of FIG. 8B.
Figure 8D:
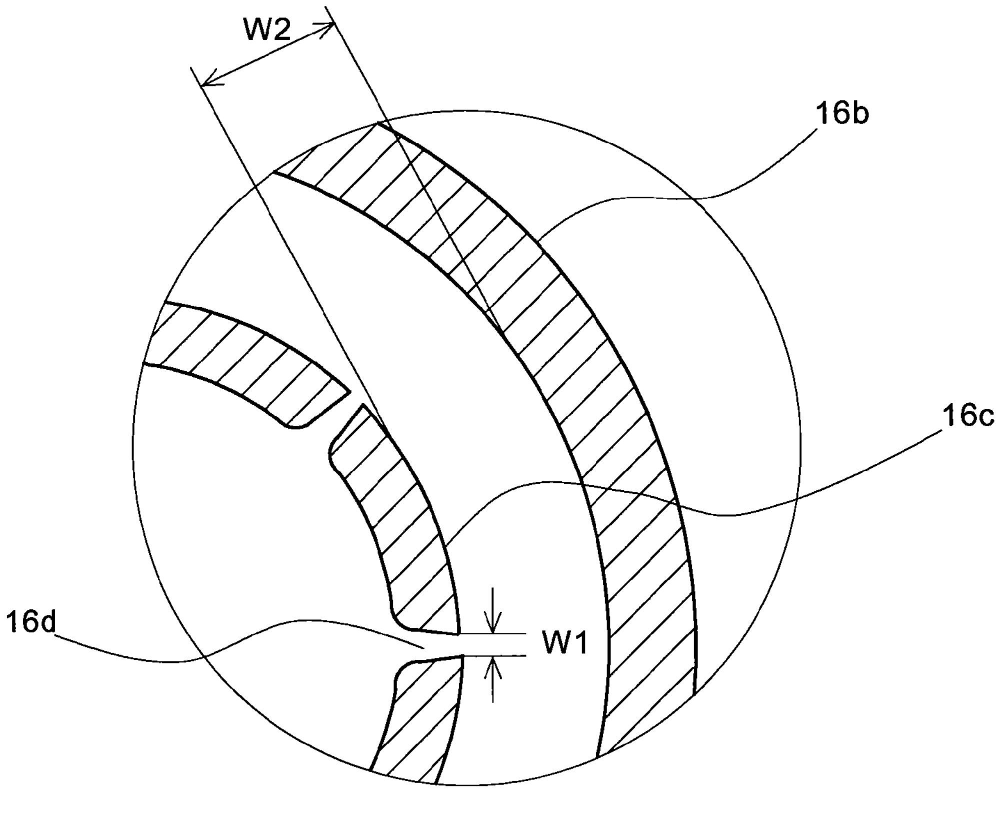
FIG. 8D is an enlarged view of a part of FIG. 8C.
Figure 9A:
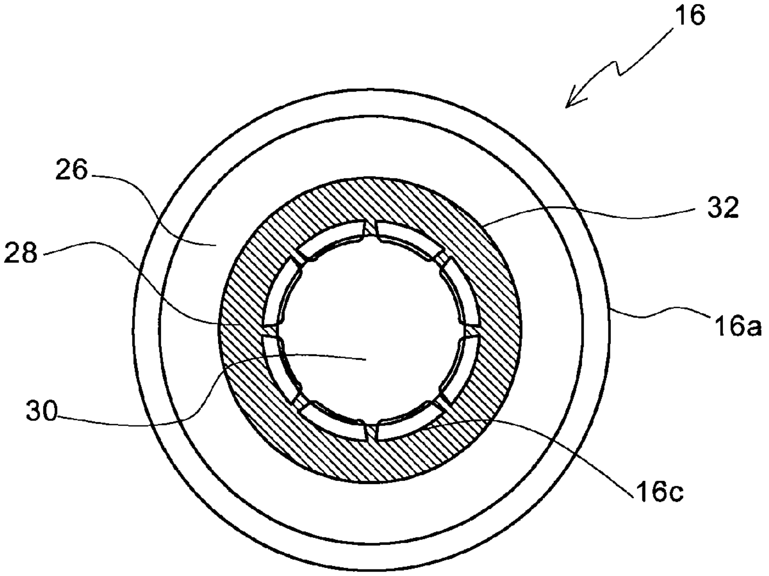
FIG. 9A is an enlarged plan view showing a state that a small quantity of liquid is fed into the preferred embodiment of the fluid handling unit according to the present invention, which corresponds to FIG. 8A.
Figure 9B:
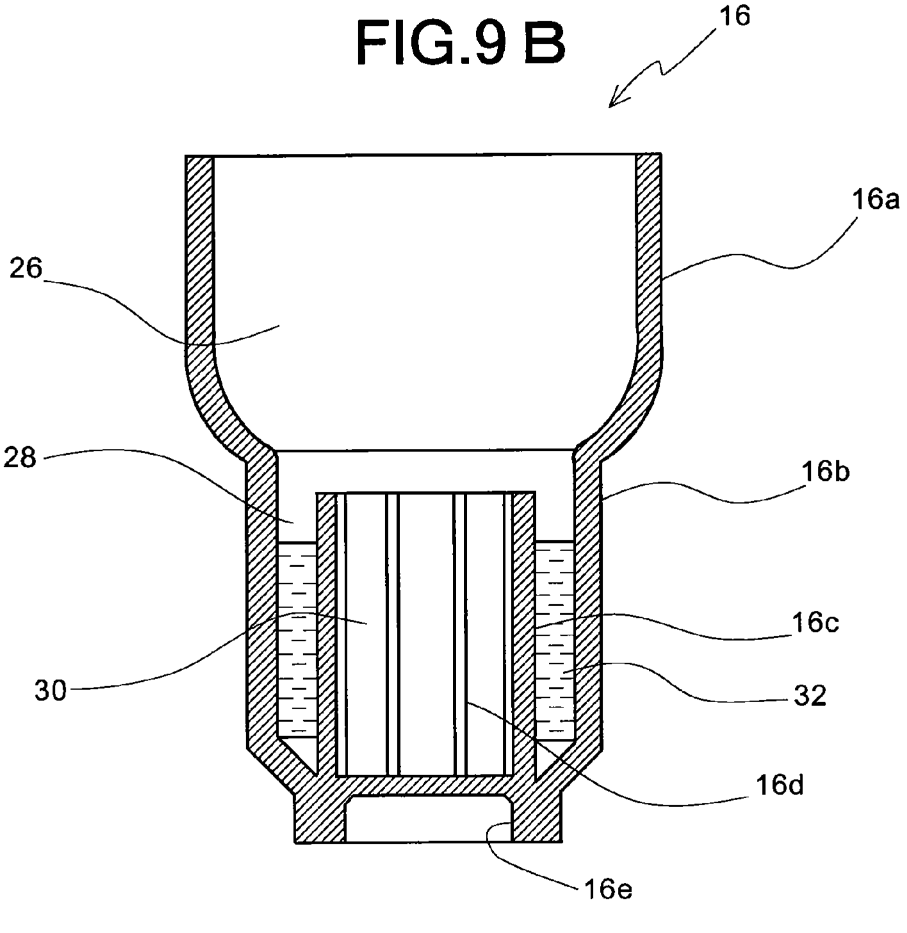
FIG. 9B is a sectional view showing a state that a small quantity of liquid is fed into the preferred embodiment of the fluid handling unit according to the present invention, which corresponds to FIG. 8B.

FIGS. 6 through 9B are enlarged views showing one of the fluid handling units 16, each of which is mounted in a corresponding one of the mounting recessed portions 14 of the fluid handling apparatus 10 in this preferred embodiment. FIG. 6 is a plan view of one of the fluid handling units 16, each of which is mounted in a corresponding one of the mounting recessed portions 14 of the fluid handling apparatus 10, and FIG. 7 is a sectional view taken along line VII-VII of FIG. 6. FIG. 8A is a plan view of one of the fluid handling units 16 of the fluid handling apparatus 10 in this preferred embodiment, and FIG. 8B is a sectional view taken along line VIIIB-VIIIB of FIG. 8A. FIG. 8C is a sectional view taken along line VIIIC-VIIIC of FIG. 8B, and FIG. 8D is an enlarged view of a part of FIG. 8C. FIGS. 9A and 9B show a state that a small quantity of liquid is fed into the fluid handling unit 16, FIG. 9A being a plan view corresponding to FIG. 8A, and FIG. 9B being a sectional view corresponding to FIG. 8B.

Each of the fluid handling units 16 is made of a resin material, such as polystyrene (PS), polycarbonate (PC) or polymethyl methacrylate (PMMA). As shown in FIGS. 6 through 8B, each of the fluid handling units 16 substantially has the same height as the depth of the corresponding one of the mounting recessed portions 14, and comprises an outside large-diameter cylindrical portion 16*a*, an outside small-diameter cylindrical portion 16*b* and an inside cylindrical portion 16*c* which are integral-molded so as to be integrated with each other.

The outside large-diameter cylindrical portion 16*a* is a substantially cylindrical portion which has a half height of the corresponding one of the fluid handling units 16 and which has an outside diameter being substantially equal to the inside diameter of the corresponding one of the mounting recessed portions 14. The outside large-diameter cylindrical portion 16*a* is designed to be fitted into the corresponding one of the mounting recessed portions 14 to be fixed thereto when each of the fluid handling units 16 is inserted into the corresponding one of the mounting recessed portions 14 to be mounted therein. The bottom end portion of the outside large-diameter cylindrical portion 16*a* is curved and inclined inwardly downwards to extend to the outside small-diameter cylindrical portion 16*b* to be connected to the upper end portion of the outside small-diameter cylindrical portion 16*b*.

The outside small-diameter cylindrical portion 16*b* is a substantially cylindrical portion which has a half height of the corresponding one of the fluid handling units 16 and which has a smaller outside diameter than that of the outside large-diameter cylindrical portion 16*a*. The outside small-diameter cylindrical portion 16*b* extends in the same axial directions as those of the outer large-diameter cylindrical portion 16*a*. The bottom end portion of the outside small-diameter cylindrical portion 16*b* has a portion inclined inwardly downwards. From the bottom end of this portion inclined inwardly downwards, a bottom face portion extends in directions substantially perpendicular to the axial directions of the outside small-diameter cylindrical portion 16*b*. The underside of the bottom face portion of the outside small-diameter cylindrical portion 16*b* has a recessed portion 16*e* having a diameter which is substantially equal to the inside diameter of the inside cylindrical portion 16*c*.

The inside cylindrical portion 16*c* is a substantially cylindrical portion which extends upwards in the same axial directions as those of the outside small-diameter cylindrical portion 16*b* from the upper face of the bottom face portion of the outside small-diameter cylindrical portion 16*b*. The height of the upper end of the inside cylindrical portion 16*c* is lower than the upper portion of the outside small-diameter cylindrical portion 16*b*, and the outside diameter of the inside cylindrical portion 16*c* is smaller than the inside diameter of the outside small-diameter cylindrical portion 16*b*. The inside cylindrical portion 16*c* has a plurality of slits 16*d* (eight slits 16*d* in this preferred embodiment) which extend substantially linearly in substantially parallel to each other from the bottom end of the inside cylindrical portion 16*c* to the upper end thereof. The plurality of slits 16*d* pass through the inside cylindrical portion 16*c*, and are arranged at regular intervals in circumferential directions thereof. The width of each of the slits 16*d* is a few micrometers to hundreds micrometers, and the width of each of the slits 16*d* on the side of the inside face of the inside cylindrical portion 16*c* is larger than that on the side of the outside face thereof.

Furthermore, in the outside large-diameter cylindrical portion 16*a*, a space serving as an injecting section 26 for injecting a fluid, such as a liquid sample, is formed. Between the outside small-diameter cylindrical portion 16*b* and the inside cylindrical portion 16*c*, there is formed an outside fluid housing chamber 28 (having a volume of, e.g., not larger than about 30 μl) which is a substantially annular space capable of being used as a reaction chamber. In the inner cylindrical portion 16*c*, there is formed an inside fluid housing chamber 30 which is a substantially cylindrical chamber capable of being used as a measuring chamber.

If a small quantity (e.g., not larger than about 30 μl) of liquid, such as a reagent, is fed into the injecting section 26, the liquid is fed into one or both of the inside fluid housing chamber 30 and the outside fluid housing chamber 28. Since the capillary rise (the height of the liquid level raised by capillary force) Z is expressed by $Z=2T\cos\theta/\gamma\cdot r\cdot g$ (θ: contact angle, T: surface tension, γ: liquid density, r: capillary radius, g: gravitational acceleration), the capillary force exerted on the liquid in the outside fluid housing chamber 28, which has a smaller width in radial directions than the diameter of the inside fluid housing chamber 30, is greater than the capillary force exerted on the liquid in the inside fluid housing chamber 30. Therefore, as shown in FIGS. 9A and 9B, the most part of the liquid fed into the injecting section 26 is drawn into the outside fluid housing chamber 28 due to capillarity, and is held in the outside fluid housing chamber 28 as shown by reference number 32. Thus, the width W1 of each of the slits 16*b* formed in the inside cylindrical portion 16*c*, and the width W2 of the substantially annular outside fluid housing chamber 28 (the difference between the inside diameter of the outside small-diameter cylindrical portion 16*b* and the outside diameter of the inside cylindrical portion 16*c*) may be suitably determined so that the most part of the liquid fed into the injecting section 26 is drawn into the outside fluid housing chamber 28.

Furthermore, after the most part of the liquid fed into the injecting section 26 is accumulated in the outside fluid housing chamber 28, if the total quantity of the liquid exceeds a predetermined quantity (e.g., about 30 μl) by additionally feeding the liquid into the injecting section 26, the liquid flows into the inside cylindrical portion 16*c* via the opening of the top end of the inside cylindrical portion 16*c* and/or the slits 16*d*, so that the liquid can be filled in the outside fluid housing chamber 28 and the interior of the inside cylindrical portion 16*c* to entirely extend in the fluid handling unit 16.

Thus, according to the fluid handling unit 16 in this preferred embodiment, if a small quantity of liquid, such as a reagent, is fed into the injecting section 26, the most part of the liquid fed into the injecting section 26 is drawn into the outside fluid housing chamber 28, and flows in circumferential directions in the outside fluid housing chamber 28 to be held in the outside fluid housing chamber 28. Therefore, even if the outside fluid housing chamber 28 is used as a reaction chamber to detect a specimen by a small quantity of reagent, it is possible to greatly increase the height of the liquid level to increase the surface area of a reaction wall surface (the inner wall surface of the outside fluid housing chamber 28), and it is possible to decrease the distance between the specimen and the reaction wall surface. Thus, it is possible to improve the reaction efficiency to shorten the reaction time, and it is possible to decrease the quantity of the used reagent to reduce the costs.

According to the fluid handling unit 16 in this preferred embodiment, even if the quantity of a reagent for use in analysis is very small, the reagent can be stably held in the outside fluid housing chamber 28 serving as a reaction chamber, so that it is possible to further improve the accuracy of analysis. Moreover, if the quantity of available specimen is very small so that the concentration of the specimen in a solution containing the specimen is very low, there are some cases where conventional microwell plates can not obtain stable results of analysis since the specimen in the solution can not reach the reaction part of the wall surface of wells. However, the fluid handling unit 16 in this preferred embodiment can stably feed a specimen into the outside fluid housing chamber 28 serving as a reaction chamber, so that it is possible to further improve the accuracy of analysis in comparison with conventional microwell plates.

According to the fluid handling unit 16 in this preferred embodiment, a reagent fed into the inside fluid housing chamber 30 from the injecting section 26 is drawn into the outside fluid housing chamber 28 to be held therein even if the reagent is not fed along the inner wall of the injecting section 26 in order to feed the reagent into the outside fluid housing chamber 28. Therefore, the reagent is automatically moved into the outside fluid housing chamber 28 to be held therein regardless of the reagent feeding position, so that it is possible to easily carry out the operation for feeding the reagent.

Furthermore, if the width of each of the slits 16*d* on the side of the inside face of the inside cylindrical portion 16*c* is larger than that on the side of the outside face thereof as the fluid handling unit 16 in this preferred embodiment, the liquid level in the outside fluid housing chamber 28 can be substantially flat. In addition, even if the quantity of a liquid, such as a reagent, fed into the injecting section 26 is small (not larger than the volume of the outside fluid housing chamber 28), the variation in area of the liquid contacting the inner wall surface of the outside fluid housing chamber 28 can be suppressed between a plurality of fluid handling units 16 and between measuring operations.

Moreover, according to the fluid handling unit 16 in this preferred embodiment, after a sufficient quantity of cleaning solution is fed into the injecting section 26 to be filled in the interior of the fluid handling unit 16 (the interiors of the injecting section 26, outside fluid housing chamber 28 and inside fluid housing chamber 30), it is possible to easily discharge the cleaning solution. Therefore, the fluid handling unit 16 in this preferred embodiment has excellent cleaning performance, and can lower background during measurement. In addition, since the height of the upper end of the inside cylindrical portion 16*c* is lower than the upper end of the outside large-diameter cylindrical portion 16*a*, a sufficient quantity of cleaning solution can be fed into the injecting section 26 to float components to be removed, so that the components can be discharged by means of a pipette or the like. Therefore, the fluid handling unit 16 in this preferred embodiment has more excellent cleaning performance than that when the height of the upper end of the inside cylindrical portion 16*c* is equal to the height of the upper end of the outside large-diameter cylindrical portion 16*a*.

Figure 12:
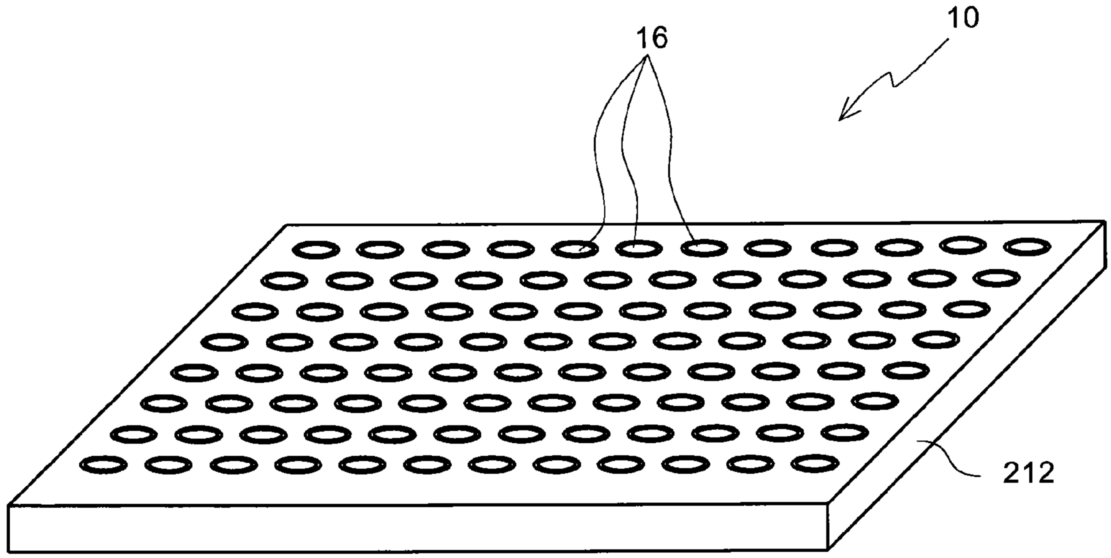
FIG. 12 is a perspective view of a modified example of a fluid handling apparatus according to the present invention.

Furthermore, the fluid handling unit 16 in this preferred embodiment can be integral-molded by injection molding or the like, so that it can be easily produced. As a modified example of a fluid handling apparatus 10 in this preferred embodiment, a supporting member 13 may be integral-molded by injection molding or the like so as to have a plurality of fluid handling units 16 arranged at regular intervals in a row. Alternatively, as shown in FIG. 12, a plate-shaped apparatus body 212 may be integral-molded by injection molding or the like so as to have a plurality of fluid handling units 16 arranged as a matrix without providing any fluid handling unit supporting members.

Figure 10A:
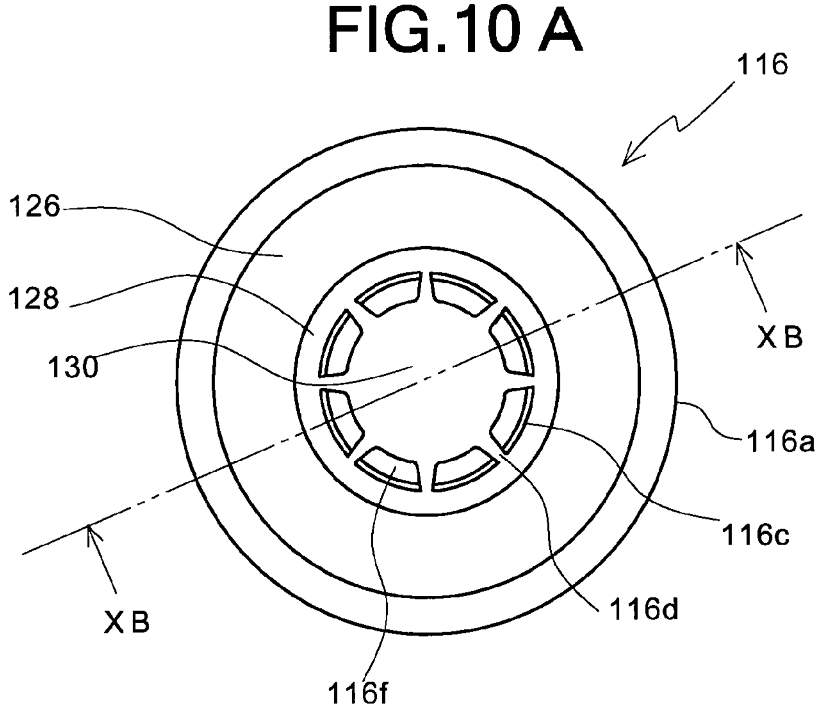
FIG. 10A is an enlarged plan view of a modified example of the fluid handling unit shown in FIGS. 8A through 8D.
Figure 10B:
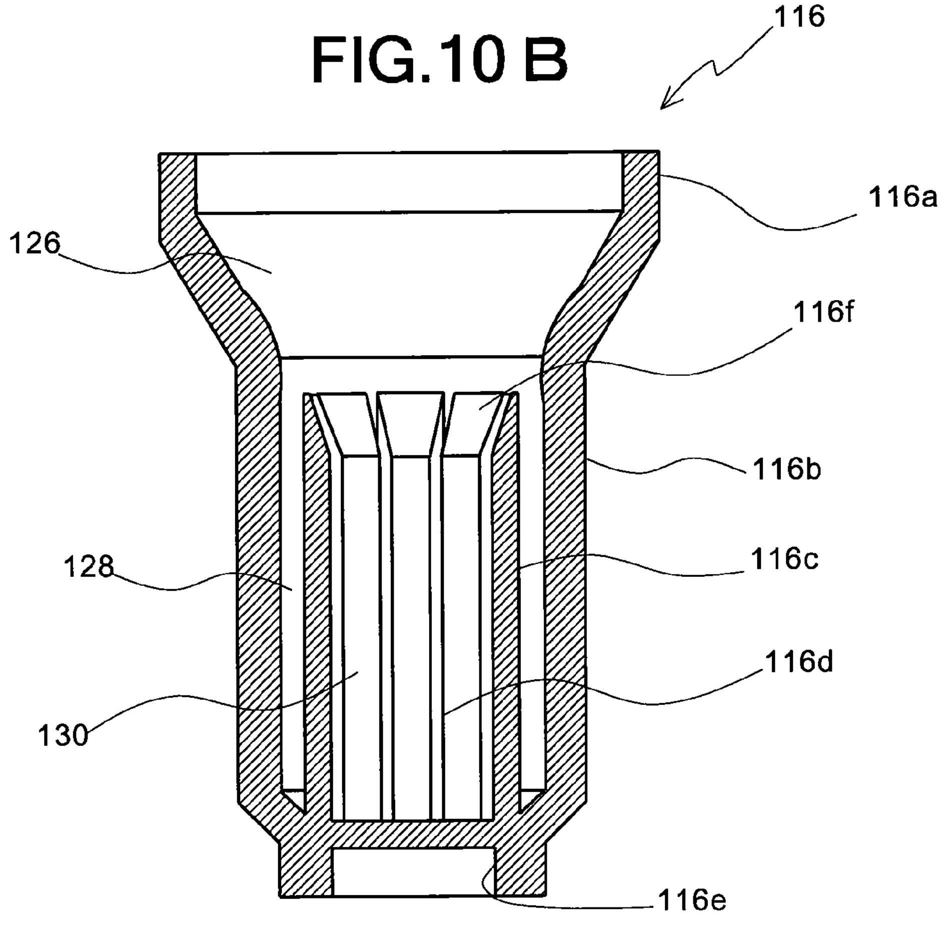
FIG. 10B is a sectional view taken along line XB-XB of FIG. 10A.

FIGS. 10A and 10B show a modified example of a fluid handling unit 16 in this preferred embodiment. The fluid handling unit 116 in this modified example substantially has the same structure as that of the fluid handling unit 16, except that the upper end face of an inside cylindrical portion 116*c* is inclined inwardly downwards. Therefore, 100 is added to the reference numbers given to the same structural portions as those of the fluid handling unit 16 to omit the duplicate descriptions thereof. If the upper end face of the inside cylindrical portion 116*c* is inclined inwardly downwards to form an inclined surface 116*f* as this modified example, the tip portion of a pipette chip is smoothly led into an inside fluid housing chamber 130 even if the tip portion of the pipette chip hits against the upper end of the inside cylindrical portion 116*c* when a liquid is fed into the fluid handling unit 116 by means of the pipette chip. Therefore, it is possible to prevent the inside cylindrical portion 116*c* from being deformed and broken by collision of the pipette chip with the inside cylindrical portion 116*c*.

As an example of a fluid handling unit 16 in this preferred embodiment, an example of a fluid handling unit used as a sample analyzing unit will be described below.

First, 100 μl of anti-TNF-α antibody was fed into the injecting portion 26 of the fluid handling unit 16 to be held at 25° C. for two hours to immobilize a capturing (or catching) antibody on the inner wall of the fluid handling unit 16. Thereafter, 170 μl of a cleaning solution (PBS-0.02% Tween 20) was fed into the injecting section 26, and then, discharged to clean the interior of the fluid handling unit 16.

Then, after 170 μl of a blocking solution (PBS-1% BSA) was fed into the injecting section 26 to be held at 4° C. for 16 hours to block the inner wall of the fluid handling unit 16, and the blocking solution was discharged.

Then, 100 μl of TNF-α antibody was fed into the injecting section 26 to be held at 25° C. for one hour to cause an antigen reaction (specimen reaction). Thereafter, 170 μl of a cleaning solution (PBS-0.02% Tween 20) was fed into the injecting section 26, and then, discharged to clean the interior of the fluid handling unit 16.

Then, 100 μl of an antibody labeled with biotin was fed into the injecting section 26 to be held at 25° C. for one hour to cause a detecting antibody reaction. Thereafter, 170 μl of a cleaning solution (PBS-0.02% Tween 20) was fed into the injecting section 26, and then, discharged to clean the interior of the fluid handling unit 16.

Then, 100 μl of an enzyme (HRP Peroxidase Streptavidin) was fed into the injecting section 26 to be held at 25° C. for twenty minutes to cause an enzyme reaction. Thereafter, 170 μl of a cleaning solution (PBS-0.02% Tween 20) was fed into the injecting section 26, and then, discharged to clean the interior of the fluid handling unit 16.

Then, 50 μl of a substrate (TMB) was fed into the injecting section 26 to be held at 25° C. for ten minutes to cause a substrate reaction, and then, 50 μl of a reaction stop solution (1N HCl) was fed into the injecting section 26 to stop the reaction. Then, the inside fluid housing chamber 30 was irradiated with light having a wavelength of 450 nm in a longitudinal direction (in a vertical direction) to measure the intensity of absorbance of a reaction solution in the inside fluid housing chamber 30.

As a comparison example, a substantially cylindrical well having the same shape as that of the mounting recessed portion 14 of the fluid handling apparatus 10 in this preferred embodiment was used for carrying out the same measurement.

Figure 11:
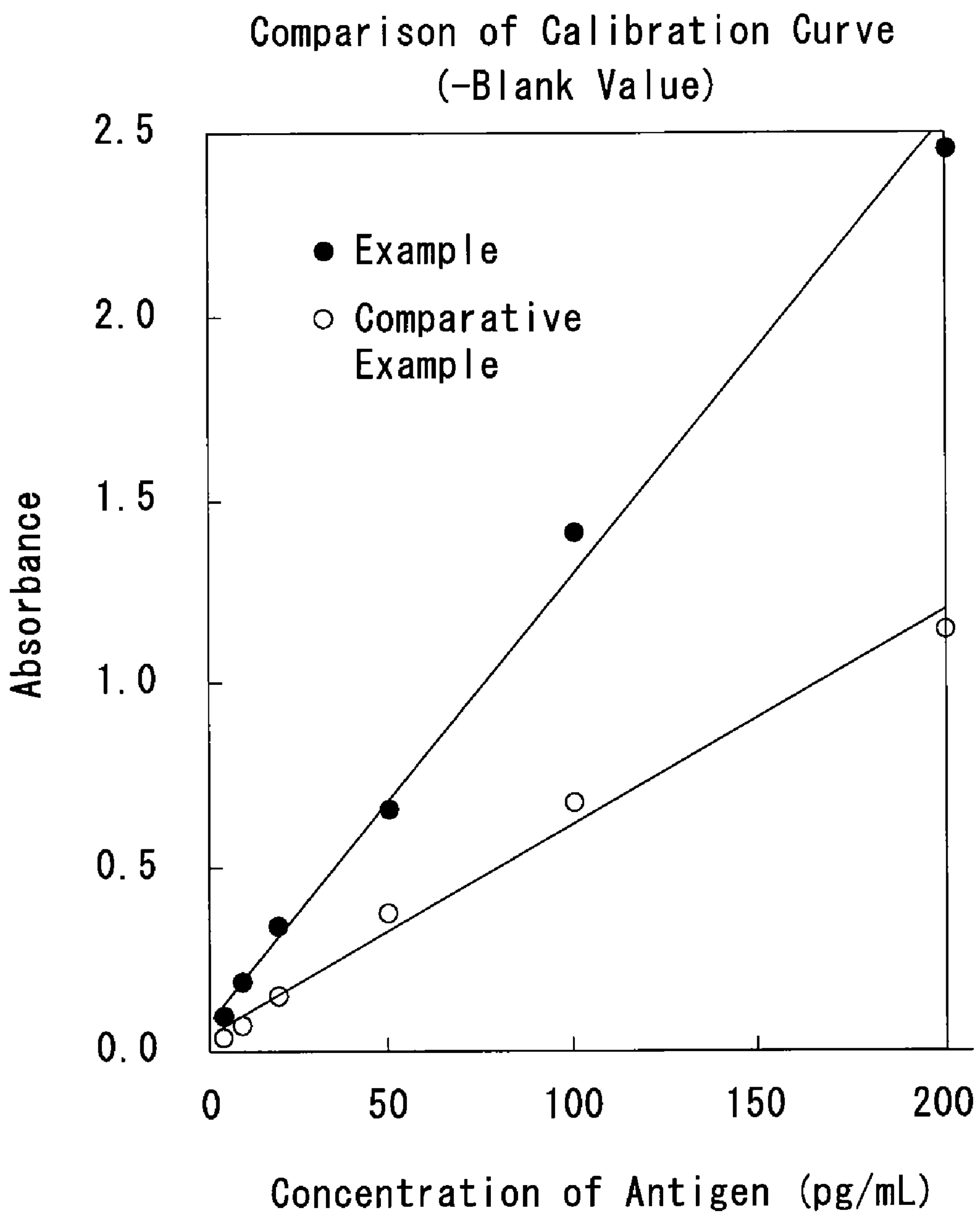
FIG. 11 is a graph showing the results of absorbance measured in Example and Comparative Example.

As a result, it can be seen from in FIG. 11 that the absorbance in Example, in which the fluid handling unit 16 in this preferred embodiment is used, is twice or more of that in Comparative Example. Thus, it is possible to greatly enhance the intensity of measurement even if the quantity of liquid (the quantity of a capturing (or catching) antibody, an antigen serving as a specimen, a detecting antibody or the like) is substantially equal to that in Comparative Example, and it is possible to obtain the intensity of measurement, which is substantially equal to that in Comparative Example, even if the quantity of liquid is far smaller than that in Comparative Example.

While the present invention has been disclosed in terms of the preferred embodiment in order to facilitate better understanding thereof, it should be appreciated that the invention can be embodied in various ways without departing from the principle of the invention. Therefore, the invention should be understood to include all possible embodiments and modification to the shown embodiments which can be embodied without departing from the principle of the invention as set forth in the appended claims.

What is claimed is:

1. A fluid handling unit comprising:

an container body having a bottom portion and a side portion for forming a fluid housing section therein, said container body having an opening at an upper end thereof;

a partition wall portion which extends from the bottom portion for dividing the fluid housing section of the container body into a first fluid housing chamber and a second fluid housing chamber; and a communication passage which passes through the partition wall portion to establish a communication between the first fluid housing chamber and the second fluid housing chamber, wherein the communication passage is associated with the first and second fluid housing chambers for causing a liquid in the first fluid housing chamber to enter the second fluid housing chamber due to capillarity while preventing the liquid in the second fluid housing chamber from entering the first fluid housing chamber when the quantity of the liquid fed into the fluid housing section from the opening of the container body is not larger than a predetermined quantity, and for allowing the liquid in the second fluid housing chamber to enter the first fluid housing chamber when the quantity of the liquid fed to the fluid housing section from the opening of the container body exceeds the predetermined quantity, and wherein said communication passage comprises a plurality of slits, and the width of each of said slits on the side of said first fluid housing chamber is larger than that on the side of said second fluid housing chamber.

2. A fluid handling unit as set forth in claim 1, wherein the height of said partition wall portion is lower than the height of said side portion of said container body.

3. A fluid handling unit as set forth in claim 1, wherein said slits pass through said partition wall portion and which extend from the bottom end of the partition wall portion to the upper end thereof.

4. A fluid handling unit as set forth in claim 1, wherein said first fluid housing chamber is surrounded by said second fluid housing chamber.

5. A fluid handling unit as set forth in claim 4, wherein said container body has a substantially cylindrical shape, and said partition wall portion has a substantially cylindrical shape which is substantially coaxial with said container body.

6. A fluid handling unit as set forth in claim 5, wherein said container body has a substantially cylindrical large-diameter portion and a substantially cylindrical small-diameter portion which is arranged below the substantially cylindrical large-diameter portion, and said partition wall portion is arranged inside of said substantially cylindrical small-diameter portion.

7. A fluid handling unit as set forth in claim 5, wherein said plurality of slits are arranged at regular intervals in circumferential directions of said partition wall portion.

8. A fluid handling unit as set forth in claim 4, wherein said partition wall portion has an upper end face which is inclined inwardly downwards.

9. A fluid handling unit as set forth in claim 1, wherein said first fluid housing chamber has a bottom face, and said second fluid housing chamber has an inclined bottom face which is inclined downwards as a distance from said first fluid housing chamber decreases, the lowest portion of the inclined bottom face of said second fluid housing chamber being substantially leveled with the bottom face of said first fluid housing chamber.

10. A fluid handling unit as set forth in claim 1, wherein the most part of the liquid in said first fluid housing chamber enters said second fluid housing chamber when the quantity of the liquid fed into said fluid housing section from said opening of said container body is not larger than said predetermined quantity.

11. A fluid handling unit as set forth in claim 1, wherein said fluid handling unit is integral-molded.

12. A fluid handling unit as set forth in claim 1, wherein said communication passage causes the liquid in said first fluid housing chamber to enter said second fluid housing chamber while preventing the liquid in said second fluid housing chamber from entering said first fluid housing chamber, by a difference between a capillary force exerted in said first fluid housing chamber and a capillary force exerted in said second fluid housing chamber, when the quantity of the liquid fed into said fluid housing section from said opening of said container body is not larger than said predetermined quantity.

13. A fluid handling unit as set forth in claim 12, wherein said capillary force exerted in said second fluid housing chamber is greater than said capillary force exerted in said first fluid housing chamber.

14. A fluid handling apparatus comprising:

an apparatus body; and a plurality of fluid handling units arranged on said apparatus body, wherein each of said plurality of fluid handling units is a fluid handling unit as set forth in claim 1.

15. A fluid handling apparatus as set forth in claim 14, wherein said plurality of fluid handling units are arranged on said apparatus body as a matrix.

16. A fluid handling apparatus as set forth in claim 14, wherein said plurality of fluid handling units, together with said apparatus body, are integral-molded.

17. A fluid handling apparatus as set forth in claim 14, wherein said apparatus body comprises a frame and a plurality of supporting members substantially arranged on the frame in parallel, and said plurality of fluid handling units are arranged on each of said supporting members at regular intervals in a row.

18. A fluid handling apparatus as set forth in claim 17, wherein said plurality of fluid handling units, together with each of said supporting member, are integral-molded.

19. A fluid handling unit comprising:

a container body having a bottom portion and a side portion for forming a fluid housing section therein, said container body having an opening at an upper end thereof;

a partition wall portion which extends from the bottom portion for dividing the fluid housing section of the container body into an inside fluid housing chamber and an outside fluid housing chamber surrounding the inside fluid housing chamber; and a communication passage which passes through the partition wall portion to establish a communication between the inside fluid housing chamber and the outside fluid housing chamber, wherein the communication passage is associated with the inside and outside fluid housing chambers for causing a liquid in the inside fluid housing chamber to enter the outside fluid housing chamber while preventing the liquid in the outside fluid housing chamber from entering the inside fluid housing chamber, by a difference between a capillary force exerted in said inside fluid housing chamber and a capillary force exerted in said outside fluid housing chamber, when the quantity of the liquid fed into the fluid housing section from the opening of the container body is not larger than a predetermined quantity, and for allowing the liquid in the outside fluid housing chamber to enter the inside fluid housing chamber when the quantity of the liquid fed to the fluid housing section from the opening of the container body exceeds the predetermined quantity, and wherein said communication passage comprises a plurality of slits, and the width of each of said slits on the side of said insid fluid housing chamber is larger than that on the side of said outside fluid housing chamber.

20. A fluid handling unit as set forth in claim 19, wherein said container body has a substantially cylindrical shape, and said partition wall portion has a substantially cylindrical shape which is substantially coaxial with said container body.

21. A fluid handling unit as set forth in claim 19, wherein said capillary force exerted in said outside fluid housing chamber is greater than said capillary force exerted in said inside fluid housing chamber.

22. A fluid handling unit as set forth in claim 19, wherein the height of said partition wall portion is lower than the height of said side portion of said container body.

23. A fluid handling unit as set forth in claim 19, wherein said communication passage comprises one or a plurality of slits which pass through said partition wall portion and which extend from the bottom end of the partition wall portion to the upper end thereof.

24. A fluid handling unit as set forth in claim 19, wherein said inside fluid housing chamber has a bottom face, and said outside fluid housing chamber has an inclined bottom face which is inclined downwards as a distance from said inside fluid housing chamber decreases, the lowest portion of the inclined bottom face of said outside fluid housing chamber being substantially leveled with the bottom face of said inside fluid housing chamber.

* * * * *